(12) United States Patent
Nauerth

(10) Patent No.: US 9,869,738 B2
(45) Date of Patent: Jan. 16, 2018

(54) METHOD FOR DETERMINING THE POSITION OF A FERROMAGNETIC PARTICLE AND ASSOCIATED MRI SYSTEM

(71) Applicant: Bruker BioSpin MRI GmbH, Ettlingen (DE)

(72) Inventor: Arno Nauerth, Erlenbach (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 0 days.

(21) Appl. No.: 15/368,463

(22) Filed: Dec. 2, 2016

(65) Prior Publication Data

US 2017/0160362 A1    Jun. 8, 2017

(30) Foreign Application Priority Data

Dec. 2, 2015   (DE) .................. 10 2015 224 085

(51) Int. Cl.
*G01R 33/56* (2006.01)
*A61B 5/055* (2006.01)
(Continued)

(52) U.S. Cl.
CPC .......... *G01R 33/5601* (2013.01); *A61B 5/055* (2013.01); *A61B 90/39* (2016.02);
(Continued)

(58) Field of Classification Search
CPC .......... G01R 33/5601; G01R 33/56308; A61B 90/39; A61B 5/055; A61B 2090/3954; A61B 2576/00
(Continued)

(56) References Cited

U.S. PATENT DOCUMENTS 7,962,194 B2   6/2011 Martel et al.
8,187,166 B2   5/2012 Kuth et al.
(Continued)

FOREIGN PATENT DOCUMENTS

DE    10142253 C1   4/2003

OTHER PUBLICATIONS

Muir, E. et al., "Quantitative Cerebral Blood Flow Measurements Using MRI", Methods Mol. Biol. 2014; 1135: 205-211.
(Continued)

*Primary Examiner* — Melissa Koval
*Assistant Examiner* — Rishi Patel
(74) *Attorney, Agent, or Firm* — Edell, Shapiro & Finnan, LLC

(57) ABSTRACT

A method for determining the position of at least one ferromagnetic particle (30) in a liquid matrix (31) with an MRI system (50). An MRI measurement sequence (MS1, MS2) is applied (20) to a measurement volume (52) in which the particle is situated. The measurement sequence includes a plurality of individual measurements (E1, E2), during each of which there is a spatially encoding gradient switching operation, including an excitation pulse (1) and signal recording (2), via the MRI system. The measurement sequence has a multiplicity of measurement blocks (MB1, MB2), which each include one or more individual measurements and, in a pause of the spatial encoding, an intermediate gradient (ZW) switched by the MRI system. The intermediate gradients are dimensioned such that, averaged over time, the particle is kept substantially in the same position (M1, M2) over each measurement block.

20 Claims, 7 Drawing Sheets

(51) Int. Cl.
G01R 33/563 (2006.01)
A61B 90/00 (2016.01)

(52) U.S. Cl.
CPC ............... *G01R 33/56308* (2013.01); *A61B 2090/3954* (2016.02); *A61B 2576/00* (2013.01)

(58) Field of Classification Search
USPC .................................................. 324/300–322
See application file for complete search history.

(56) References Cited

U.S. PATENT DOCUMENTS

| 8,948,841 B2 | 2/2015 | Martel et al. | |
| 2014/0005522 A1* | 1/2014 | Zurovcik | A61B 10/0233 600/411 |

OTHER PUBLICATIONS

Thompson, R. et al., "Real-Time Volumetric Measurements with Complex-Difference MRI", Magn Reson Med. Dec. 2003; 50(6): 1248-1255.

Dike Action in corresponding German Application No. 102015224085.1, dated Aug. 23, 2016, along with a partial English translation.

Yang H. et al., "Interleaved Magnetic Steering and MR imaging of USPIO Particles in One Dimension: Early Results", International Society for Magnetic Resonance in Medicine, ISMRM, No. 3830, Apr. 2014, 1 page.

Munitta M. et al., "Directing cell therapy to anatomic target sites in vivo with magnetic resonance targeting", Nature Communications, vol. 6, Aug. 2015, 12 pages.

Johannes R. et al., "Targeted magnetic delivery and tracking of cells using a magnetic resonance imaging system", Biomaterials, vol. 31, No. 20, Apr. 2010, 6 pages.

Sylvain M. et al., "Interactive System for Medical Interventions Based on Magnetic Resonance Targeting", Achi 2011: The Fourth International Conference on Advances in Computer-Human Interactions, Feb. 2011, 6 pages.

* cited by examiner

METHOD FOR DETERMINING THE POSITION OF A FERROMAGNETIC PARTICLE AND ASSOCIATED MRI SYSTEM

CROSS REFERENCE TO RELATED APPLICATIONS

This application claims foreign priority under 35 U.S.C. §119(a)-(d) to German Application No. 10 2015 224 085 filed on Dec. 2, 2015, the entire contents of which are hereby incorporated into the present application by reference.

FIELD OF THE INVENTION

The invention relates to a method for determining the position of at least one ferromagnetic particle in a liquid matrix with an MRI system, with an MRI measurement sequence being applied to a measurement volume in which the particle is situated. Such a method is disclosed e.g. in U.S. Pat. No. 7,962,194 B2.

BACKGROUND

Micro-machines and micro-robots provide an option for undertaking manipulations, measurements or other functions with a high precision in structures which are difficult to access and, in particular, have small dimensions. The fields of application of micro-machines and micro-robots are diverse but are currently found predominantly in the field of production technology. However, applications in the biotechnology and medical engineering sectors are also possible. Moreover, micro-components can be used in composite materials or composite components in order to extend or improve their mechanical properties or other material properties.

A general problem relating to the use of micro-machines, micro-robots or micro-components is that of transporting them to a desired location (location of use).

Dedicated drive systems, e.g. running legs, have been disclosed for micro-robots; however, such drive systems are expensive and difficult to construct.

In the case of ferromagnetic particles, there is the option of exerting an external force thereon by way of a magnetic field gradient. As a result of this, it is possible to move the ferromagnetic particle.

In addition to the movement, the transportation to a desired location requires monitoring the current location of the ferromagnetic particle, for instance to correct the current location through further movements where necessary.

However, micro-machines, micro-robots and micro-components are often used in environments in which direct optical observation from the outside is impossible, for example because an envelope or housing blocks the observation, or else because the micro-machine, the micro-robot or the micro-component is situated in a cloudy liquid matrix. By way of example, such a cloudy liquid matrix may be a lubricating oil, a solution of non-cross-linked or partly cross-linked polymer constituents or else a slip for manufacturing ceramics. In medical fields of application, the cloudy liquid matrix may also be e.g. blood or lymph.

Magnetic resonance imaging (MRI) methods are used in diverse ways in order to obtain image information about structures. With such MRI methods, it is also possible to obtain image information from the interior of a structure without damaging the structure. By way of example, body parts of humans and animals can be imaged using such MRI methods in clinical applications.

U.S. Pat. No. 7,962,194 B2 describes a method and a system for driving and controlling the displacement of a micro-robot in a blood vessel. In one variant, the method and system determine the position of a ferromagnetic body in an object using an image recording sequence obtained with an MRI system and drive the ferromagnetic body in a desired direction to a desired target location using a magnetic field gradient generated by the MRI system, until the body has reached the desired target location. In one experimental setup, the ferromagnetic body is exposed to a liquid flow in a pipe extending through the MRI system.

However, if a magnetic particle is surrounded by a liquid matrix on the path to its location of use and needs to be moved through this liquid matrix, the position of the ferromagnetic particle in many cases cannot be reliably determined in an image recording sequence using the MRI system. The ferromagnetic particle often appears out of focus in the image and is therefore not localizable with sufficient precision in the image recording or disappears from the measurement volume altogether.

U.S. Pat. No. 8,948,841 B2 describes a method for tracking a magnetic object with an MRI system, wherein the location of the magnetic object is calculated using projections of magnetic iso-surfaces.

DE 101 42 253 C1 describes an endo-robot system which comprises a magnetic bulk field for cancelling the effect of gravity and a three-dimensional controllable gradient field for navigating the endo-robot. The endo-robot is provided for carrying out minimally invasive interventions within the body of a patient.

SUMMARY

It is an object of the present invention to facilitate a more reliable and precise determination of the position of a ferromagnetic particle in a liquid matrix. Furthermore, it is an object of the invention to propose a method and an MRI system which facilitate efficient positioning of the ferromagnetic particle in a liquid matrix.

This object is achieved by a method of the type set forth at the outset, which is characterized in that the measurement sequence comprises a plurality of individual measurements, during each of which there is a spatially encoding gradient switching operation, including an excitation pulse and signal recording, with the MRI system, and in that the measurement sequence comprises a multiplicity of measurement blocks, which each comprise one or more individual measurements and in a pause of the spatial encoding an intermediate gradient switched with the MRI system, the intermediate gradients being dimensioned such that, averaged over time, the particle is kept substantially in the same position over each measurement block.

In principle, a multiplicity of individual measurements are required to obtain sufficient information for determining the position of the ferromagnetic particle, said individual measurements being worked through in succession in a measurement sequence. A certain amount of time is allowed to elapse after each of the individual measurements in order to allow the nuclear spins to relax.

Forces act on the particle during the individual measurements and the relaxation times, in particular as a result of gravity, as a result of flows in the liquid matrix or else as a result of the spatially encoding gradient switching operations during the individual measurements. These forces attempt to displace the particle during the measurement sequence. Displacements during the measurement sequence may corrupt the information for determining the position of the ferromagnetic particle. In the worst case scenario, the particle migrates out of the measurement volume.

Within the scope of the present invention, provision is made for spatially stabilizing the ferromagnetic particle between the individual measurements by way of applying intermediate gradients in order thus to reduce or cancel a drift of the ferromagnetic particle over the measurement sequence. The intermediate gradient generates an additional force on the particle, which typically compensates the remaining external forces acting on the particle, or else cancels the effects of external forces which already occurred during the preceding individual measurements.

Within the scope of the invention, a measurement sequence is subdivided into a multiplicity of measurement blocks. Each measurement block comprises a first part, during which one or more individual magnetic resonance measurements take place in the measurement volume, and a second part, during which an intermediate gradient is switched. A respective mean position of the particle in the measurement volume emerges for each measurement block. According to the invention, the intermediate gradients of the measurement blocks are dimensioned such that the mean position of the particle is substantially the same for each individual measurement block. What this ensures is that the particle is substantially located at the same location in the measurement volume during all individual measurements of a measurement sequence.

It should be noted that, as a matter of principle, a drift of the ferromagnetic particle within an individual measurement cannot be avoided since the intermediate gradient would interfere with the spatial encoding and therefore may not be applied during the spatial encoding. Furthermore, the spatial encoding itself may also cause a drift. However, the intermediate gradient between the individual measurements is able to prevent an increase of the drift and also cancel a preceding drift. In individual cases, the drift may be so small during an individual measurement that compensation is unnecessary. In this case, the intermediate gradient may be restricted to holding the position of the particle between the individual measurements.

Preferably, the position of the particle (for example, in relation to the centre thereof) is held precisely on the pixel of the spatial encoding when averaged over time so that, when averaged over time, the position of the particle lies in the same pixel for each measurement block of the measurement sequence. However, in many cases, it is sufficient for the position of the particle to be maintained to such an extent over the various measurement blocks of the measurement sequence that the following applies over the whole measurement sequence for a drift DRZ of the particle with a (largest) diameter PG: $DRZ \leq 5*PG$, preferably $DRZ \leq 2*PG$, in relation to the distance from the initial point and end point of the particle at the start and end of the measurement sequence. At least, the intermediate gradients should ensure that the particle does not drift out of the measurement volume over the entire measurement sequence. In the exemplary case of a two-dimensional individual measurement, in which the slice thickness of the slice selection gradient is e.g. 2 mm and the image region is e.g. 30×30 mm, the drift of the particle should be no more than 1 mm in the slice direction and no more than 15 mm in the image region in relation to the image axes. Alternatively, the particle could then be sought after in adjacent slices, but this would be connected with more outlay.

In relation to a non-compensated drift DRU1 of a particle during a whole measurement sequence, which would arise without the application of intermediate gradients, the drift DRZ of the particle during the whole measurement sequence may be significantly reduced or removed completely, for example with $DRZ \leq 0.2*DRU1$, when the intermediate gradients according to the invention are applied.

The method is carried out using an MRI system, with the MM system (or the gradient coil system thereof) being used both to configure spatially encoding gradient switching operations within the scope of the individual measurements and switch the intermediate gradients with which the position of the ferromagnetic particle is stabilized over the measurement sequence. Therefore, the MRI system may advantageously be used two-fold. The method according to the invention is typically configured as an operating method on the MRI system, with a control device being programmed or configured in such a way that intermediate gradients are switched in each case between the individual measurements or groups of individual measurements of the measurement sequence.

The ferromagnetic particle may be embodied as a micro-machine, micro-robot or micro-component. A typical dimension of the ferromagnetic particle is less than one millimeter (in relation to the largest diameter), generally between 25 μm and 250 μm. The ferromagnetic particle consists partly or completely of ferromagnetic material, in particular iron, cobalt, nickel or alloys of these metals. The liquid matrix is usually based on water, a water-alcohol mixture or an organic solvent. In the case of an application in production technology, the liquid matrix may be an oil, in particular a silicone oil, or an aqueous solution, in particular an aqueous surfactant solution. For an application in materials technology, the liquid matrix may be an aqueous or organic solution of non-cross-linked or partly cross-linked polymer constituents (in particular monomers or oligomers for polycondensation) or a slip (suspension of ceramic particles). For the purposes of producing a composite material or a composite component, the liquid matrix for example rinses around and/or penetrates e.g. a basic structure which should be strengthened in a targeted manner by the ferromagnetic particle. In the case of an application in biotechnology or medicine, the liquid matrix may be e.g. blood in the blood vessel system or lymph in the lymph vessel system of an animal or human. In the body, the ferromagnetic particle may be brought to a target location by the liquid matrix, for example in order to release a medicament there or else to locally destroy body tissue by the action of heat (for example as a result of inductive heating of the ferromagnetic particle). It should be noted that such therapeutic treatment steps are not part of the claimed method.

The intermediate gradient for stabilizing the particle position is typically selected in a targeted manner in view of a calculated or measured external action of force on the particle. In individual cases, the intermediate gradient may also be optimized iteratively by way of a plurality of measurement sequences or image recordings taking place in advance, until a particle movement is minimized, in particular without calculating or measuring the external action of force on the particle as such. The latter procedure may be used, in particular, for compensating the action of gravity on the particle, which is substantially independent of location. A corresponding statement applies to a fixing gradient (see below).

Preferred Variants of the Invention

In a preferred variant of the method according to the invention, provision is made for the particle to move away from an initial point during the one or more individual measurements during a respective measurement block and for the intermediate gradient to be dimensioned such that, during the action of the intermediate gradient, the particle approximately moves back to the initial point. What this achieves is that each measurement block may start with substantially the same position of the particle.

A variant in which the particle moves under the influence of gravity and/or a flow of the liquid matrix and/or an action of the spatially encoding gradient switching operation during the one or more individual measurements is advantageous. These influences particularly frequently cause a noticeable drift of the ferromagnetic particle over the duration of an individual measurement. In general, a good position stabilization may be achieved by compensating these influences, according to which position stabilization a position may be determined with high reliability and accuracy.

A variant in which the spatially encoding gradient switching operation is balanced, and so, in total, does not contribute to a change in position of the particle during an individual measurement, is also preferred. In the case of the balanced gradient switching operation, the particle typically experiences a first force in a first direction during a first part and a second force of equal magnitude, in a second direction counter to the first direction, during a second part with the same duration as a result of the gradient switching operation. The contributions of these forces on the location of the ferromagnetic particle cancel over the entire individual measurement. In this variant, there is no need to take account of the spatially encoding gradient switching operation for stabilizing the position of the ferromagnetic particle, simplifying a correct setting of the intermediate gradient. On account of the viscosity of the liquid matrix, the particle is generally decelerated quickly again after the first part, i.e. the change in velocity of the first part has been cancelled before the second part begins, and so, in general, partial changes in position are caused independently from one another and in succession by the first part and the second part, which partial changes in position are equal but opposite.

In an alternative variant, provision is made for the spatially encoding gradient switching operation to be unbalanced, and so to contribute to a change in position of the particle during an individual measurement, and for the intermediate gradients also to compensate the contributions of the spatially encoding gradient switching operation. In this case, the spatially encoding gradient switching operation may be selected freely. The intermediate gradient is selected in terms of strength and duration in such a way that it also takes account of the contribution of the spatially encoding gradient switching operation and, in particular, undoes a corresponding displacement of the particle.

A variant which provides for flows in the liquid matrix to be measured prior to the measurement sequence, in particular prior to the introduction of the particle into the liquid matrix, said measurement rendering a contribution of the flows to a change in position of the particle during an individual measurement and/or during a pause of the spatial encoding ascertainable, and for the intermediate gradients also to compensate the contributions of the flows is also advantageous. By determining the flow conditions in advance, it is possible to calculate a suitable, compensating intermediate gradient or contribution for this in advance and then apply said intermediate gradient or contribution during the measurement sequence. For the free movement of the particle in the liquid flow, it is generally possible, to a good approximation, to assume that the particle moves with the velocity of the liquid flow. The force required for moving the particle counter to the liquid flow, depending on the relative velocity, may be determined to a good approximation (by way of example, the force may be determined by Stokes' equation in many cases for small, round particles). This force may then be applied by way of the magnetic field gradient for the required amount of time, taking into account the magnetic permeability of the particle material. As a result, it is possible to achieve a particularly high accuracy of the position stabilization. It should be noted that the influences of gravity are also typically calculated in advance and an intermediate gradient or contribution which is suitable to this end is applied during the measurement sequence. By way of example, the gravitational force can easily be determined for particles made of a uniform material from the product of the volume of the particle, the density difference between particle material and liquid matrix, and the gravitational acceleration (local magnitude of gravitational acceleration g) (approximately 9.8 N/kg).

A variant in which the intermediate gradient, at least intermittently, presses the particle against an edge structure neighbouring the liquid matrix is also preferred. The pressure action prevents further drift of the particle. If a drift of the particle during an individual measurement is unnoticeable but a noticeable drift is feared during the relaxation between individual measurements, a good position stabilization may already be achieved only by the pressure action on the particle during the action of the intermediate gradient. It should be noted that a combination of pushing back the particle and pressing the particle against an edge structure during the duration of the intermediate gradient is also possible. During pressure action, the effective force on the particle, as a sum of the action of the intermediate gradient, gravity, and flow where applicable, should be approximately perpendicular to the surface of the edge structure. The edge structure should be so secure that the edge structure is not damaged or even penetrated by pressure action on the particle. Typically, the edge structure is formed by walls of channels or containers (the channel base or the container base as well), in which the liquid matrix is arranged. By way of example, a porous solid, on which the particle should be arranged at a specific location, may also be arranged in the liquid matrix. Then, the porous solid forms an edge structure. Polymer threads or polymer webs may also form a suitable edge structure in the liquid matrix. By way of example, in the case of medical applications, the edge structure may be the wall of a blood vessel or a lymph vessel of an animal or patient. Here, the pressure action has no therapeutic effect.

A variant in which only one individual measurement is carried out during each measurement block is particularly preferred. In this case, the intermediate gradient may be used between all individual measurements, as a result of which particularly good position stabilization is facilitated. Furthermore, the intermediate gradients may be used during a particularly large proportion of the duration of the measurement sequence in order to minimize the drift of the particle. Alternatively, an intermediate gradient may, for example, only be applied in each case after two (or even more) individual measurements for example so that the gradient coils need to be switched less frequently.

A complete image of the measurement volume is generated from the results of the individual measurements of the measurement sequence in a preferred variant. In this case, a (two-dimensional or three-dimensional) image of the measurement volume, in which the particle may be seen (or else marked), may be considered after each measurement sequence. This facilitates an intuitive, quick capture of the current position of the particle and possible changes of other structures in the measurement volume can easily be identified.

In an alternative, advantageous variant, provision is made for a multiplicity of reference projections of the measurement volume without the particle to be created prior to the measurement sequence, in particular by directly recording the reference projections of the measurement volume without the particle or by calculation from a complete image recording of the measurement volume without the particle, for a multiplicity of projections of the measurement volume with the particle to be recorded with the individual measurements, and for the position of the particle to be ascertained by comparison between the recorded projections and the reference projections. As a result of this procedure, the measurement sequence may be shortened in relation to a complete image recording; the position may be determined more quickly. Preferably, the particle position ascertained by way of the projections is plotted into a complete image of the measurement volume in order also in this case to facilitate an intuitive capture of the position.

Positioning Method

The scope of the present invention also includes a method for positioning at least one ferromagnetic particle in a liquid matrix with an MRI system, comprising the following steps:
1) determining the position of the particle with the MRI system;
2) switching a positioning gradient with the MRI system, through which the position of the particle is changed, said method being characterized
in that an above-described method according to the invention is performed within the scope of step 1) for determining the position,
with a fixing gradient, via which the position of the particle is kept substantially constant, being switched with the MRI system after the end of the measurement sequence in step 1) and until the start of the application of the positioning gradient in step 2).

Within the scope of this method, the position of the particle is fixed by a fixing gradient during the evaluation phase after the completion of the measurement sequence, while the actual position information about the particle in the measurement volume is obtained from the obtained raw data from the individual measurements, and during the decision phase (also referred to as analysis), when a next iteration of the change in position is ascertained and set on the basis of the actual position information. What this ensures is that, at the start of the pending iteration of the change in position in step 2), the particle is still situated where it is also expected on account of the preceding determination of the position in step 1). In particular, the particle is unable to migrate out of the measurement volume, and therefore become lost, during the evaluation phase and the decision phase. In practical terms, as much time as is required is available for the evaluation phase and decision phase, without needing to consider a drift of the particle.

The gradient coil system of the MRI system is used in turn for the fixing gradient, as a result of which said gradient coil system obtains a third functionality (in addition to the functionalities during the spatially encoding gradient switching operation of the individual measurements and the intermediate gradients). The gradient coil system of the MRI system is likewise used for displacing the particle within the scope of step 2), as a result of which said gradient coil system also moreover obtains a fourth functionality. A control device of the MRI system is configured or programmed in an appropriate manner. In this respect, the method according to the invention also represents an operating method for the MRI system.

Preferably, the position of the particle (for example in relation to the centre thereof) is kept precisely on the pixel of the spatial encoding during the duration of action of the fixing gradient when averaged over time. However, in many cases, it is sufficient if the position of the particle during the duration of action of the fixing gradient is at least maintained to such an extent that DRF≤5*PG, preferably DRF≤2*PG, applies over the duration of action for a drift DRF of the particle with the (largest) particle diameter PG, in relation to the distance from the initial point and end point of the particle at the beginning and end of the measurement sequence. At least, the particle should be kept in the measurement volume during the duration of action of the fixing gradient. In relation to a non-compensated drift DRU2 of a particle, which would arise between the end of the measurement sequence and the beginning of the application of the positioning gradient without application of the fixing gradient, the drift DRF of the particle during the same time may be significantly reduced or removed completely, for example with DRF≤0.2*DRU2, when the fixing gradient according to the invention is applied.

In a preferred variant of said method, steps 1) and 2) are repeated a number of times. As a result, a particle can be brought very exactly to a desired location step-by-step (iteratively).

A variant in which the particle experiences a force under the action of the fixing gradient, said force being equal and opposite to the action of gravity and, where necessary, of a flow of the liquid matrix, is advantageous. Accordingly, a particle situated in the liquid matrix may be kept in a floating manner during the action of the fixing gradient. An interaction with an edge structure is not required in this procedure, and so this variant may also be used if no suitable (in particular close-by and robust) edge structures are available.

A variant in which the fixing gradient presses the particle against an edge structure neighbouring the liquid matrix is likewise advantageous. In this case, the particle is also held by the edge structure. This procedure is also possible if the action of gravity and/or the flow conditions in the liquid matrix are not known or only known imprecisely. Preferably, the particle is moved with only a short distance from the edge structure (for example at a distance of up to one particle diameter), such that the position of the particle may readily remain substantially unchanged when resting against the edge structure. Typical suitable edge structures are porous solids or polymer strands or channel walls. In the case of medical applications, the edge structure may be, for example, the wall of a blood vessel or a lymph vessel of an animal or patient.

In the case where the particle is held against an edge structure by the fixing gradient, it may be necessary for the subsequent positioning gradient not to cause only a linear change in position. It may be necessary for the movement of the particle to initially be away from the wall and then in a specific direction, with changes in direction also being possible. This means that the positioning gradient in terms of field strength and field direction may change over time. Hence, the particle may also be moved over a curved positioning trajectory.

MRI System According to the Invention

The scope of the present invention furthermore includes an MRI system, comprising a magnet for generating a homogeneous magnetic field $B_0$ in a measurement volume, a gradient coil system for generating spatially encoding magnetic field gradients in the measurement volume and a radiofrequency excitation and readout coil system for radiating radiofrequency pulses into the measurement volume and for reading the measurement volume, which is characterized
in that the MRI system is configured to determine the position of a ferromagnetic particle according to an above-described method for determining the position according to the invention, a control device being present, the latter switching intermediate gradients between individual measurements of a measurement sequence with the gradient coil system,
and in that the MRI system is further configured to position the ferromagnetic particle according to an above-described positioning method according to the invention, the control device, with the gradient coil system, switching fixing gradients between the end of measurement sequences and the application of positioning gradients. The MRI system or the control device has appropriate programming which switches intermediate gradients between individual measurements or groups of individual measurements of a measurement sequence and which switches fixing gradients between measurement sequences and the application of subsequent positioning gradients. The MRI system according to the invention may be used accordingly in one of the above-described methods according to the invention for determining the position and the positioning. An exact position control and position correction of ferromagnetic particles is possible in a simple manner with the MRI system.

A preferred embodiment of the MRI system according to the invention provides for the gradient coil system of the MRI system to comprise a first coil subsystem for generating a magnetic field gradient in a vertical direction and at least one second coil subsystem for generating a magnetic field gradient in a horizontal direction, and for the first coil subsystem to have a maximum generable gradient strength $|G_{max}^1|$ which is greater than a maximum generable gradient strength $|G_{max}^2|$ of the second coil subsystem, preferably with $|G_{max}^1| \geq 1.5*|G_{max}^2|$. In this embodiment, the first coil subsystem is configured to be particularly strong in order to be able to compensate and, where necessary, overcompensate gravity acting in the vertical direction. The force outlay for compensating gravity, particularly in the case of fully metallic particles with conventional MRI systems, may be significant, particularly in the case of liquids with a low viscosity, and may require a comparatively high magnetic field gradient strength. Inexpedient conditions may also be handled by a strengthened first coil subsystem. Usually, a third coil subsystem is also provided for generating a magnetic field gradient in a further horizontal direction, with the horizontal direction and the further horizontal direction being orthogonal to one another. Then, typically, $|G_{max}^1|$ is also greater than a maximum generable gradient strength $|G_{max}^3|$ of the third coil subsystem, preferably with $|G_{max}^1| \geq 1.5*|G_{max}^3|$. The first coil subsystem typically has a greater number of coils and/or a higher winding number and/or a higher conductor cross section (for a higher current carrying capacity) than the other coil subsystem or subsystems in order to obtain the higher maximum gradient strength.

Furthermore, an embodiment, in which the gradient coil system of the MRI system, in particular the first coil subsystem, comprises a main part and an additional part, is advantageous, the control device being configured to switch spatially encoding gradient switching operations, intermediate gradients, fixing gradients and/or positioning gradients with the main part, and only to switch intermediate gradients, fixing gradients and/or positioning gradients, but not spatially encoding gradient switching operations, with the additional part. Additional force on the particle, in particular additional force sufficient to compensate gravity and/or flows in the liquid matrix, may be provided by the additional part for the intermediate gradients, fixing gradients and positioning gradients. In principle, the additional part may also be added to the second and/or third coil subsystem. The additional part may be arranged separately from the main part and may also be retrofitted to an existing MRI system. In a first variant, intermediate gradients, fixing gradients and positioning gradients are only generated by the additional part, and not by the main part. Only the main part, but not the additional part, is used for the spatially encoding gradient switching operation. This allows independent control circuits for the actuation of the spatially encoding gradient switching operation on the one hand and the actuation of the intermediate gradients, fixing gradients and positioning gradients on the other hand; this is particularly suitable for retrofitting an existing MRI system. In a second variant, the additional part is used for holding the particle in one position, i.e. for the exact compensation of external forces (holding gradients; GG, GF, see below). By way of example, the action of gravity on the particle may be compensated by the switched additional part ("floating particle"). Independently thereof, the main part then controls a movement of the particle (GZ, GV, see below). Controlling the movement of the particle is then decoupled from the position stabilization and is correspondingly simple; in particular, a particle may be moved equally efficiently in the vertical direction and in the horizontal direction. The main part is also used for the spatially encoding gradient switching operation, but the additional part is not. Moreover, further variants are also conceivable. In general, the main part assumes at least the spatially encoding gradient switching operation and the additional part does not take part in relation to individual measurements or the spatially encoding gradient switching operation.

Further advantages of the invention emerge from the description and the drawing. The features mentioned above and the features yet to be explained below may, according to the invention find use on their own in each case or together in arbitrary combinations. The shown and described embodiments should not be understood to be a complete list but, instead, have an exemplary character for explaining the invention.

BRIEF DESCRIPTION OF THE DRAWINGS

The invention is depicted in the drawing and explained in more detail on the basis of exemplary embodiments. In particular.

DETAILED DESCRIPTION

Overview of the Invention

Figure 1:
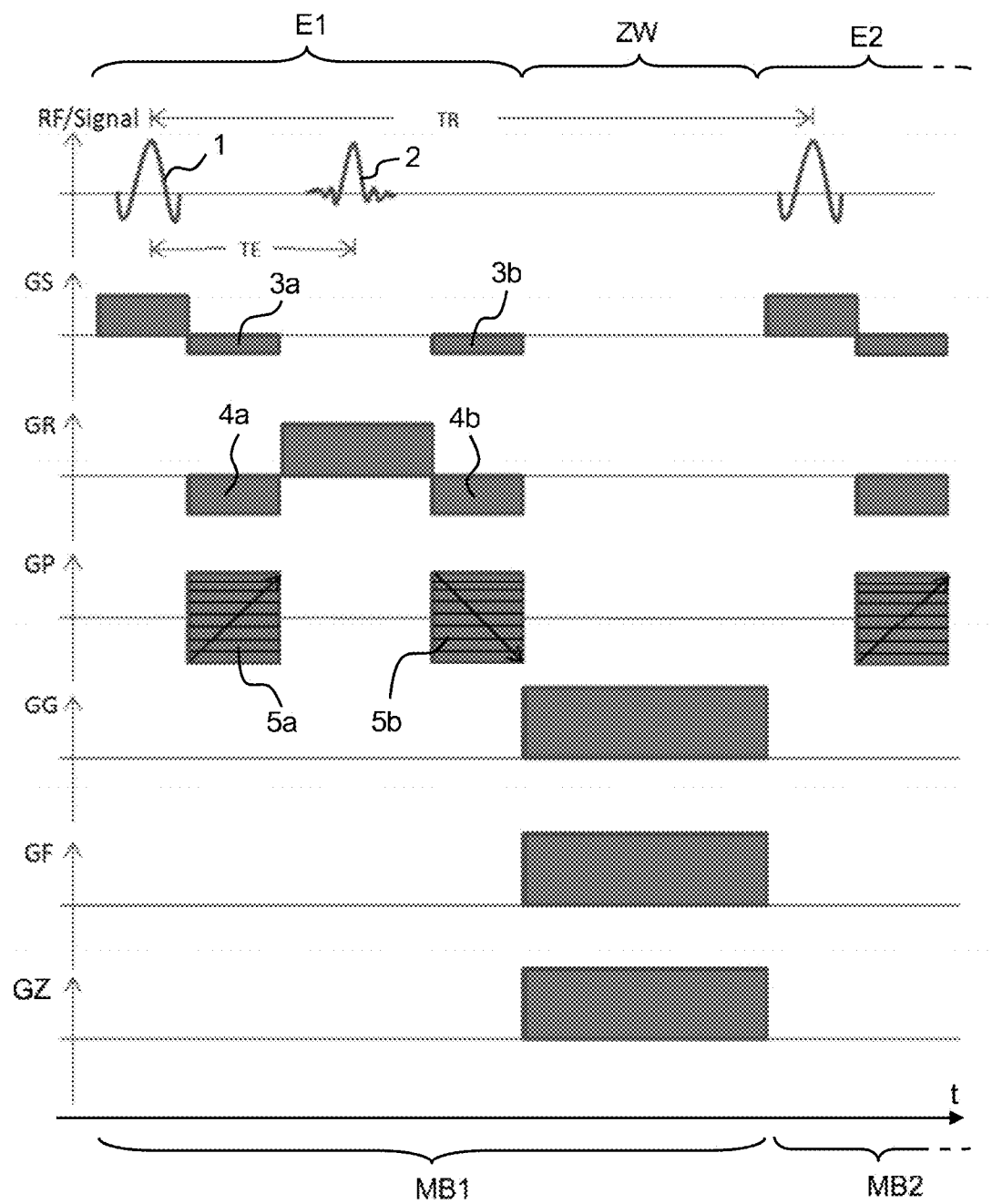
FIG. 1 shows a schematic illustration of applied gradients during a measurement sequence within the scope of the invention, in a variant with a balanced gradient switching operation.

The present invention relates to a method for an improved determination of the position of a ferromagnetic particle (object) in a liquid matrix, in particular a viscous matrix with a viscosity of 2 mPa*s or more, or else 3 mPa*s or more, using a magnetic resonance imaging (MRI) system. The present invention further relates to a method for positioning and holding the ferromagnetic particle (object) using the magnetic field gradients of the MRI system. With the aid of the MRI system, the particle may be made visible at the same time, and so visual real-time monitoring of the particle is obtained.

A possible application of the invention lies in controlling ferromagnetic objects in a human or animal body utilizing magnetic field gradients in order to guide the ferromagnetic objects to defined target positions within the body.

Under normal circumstances, the gradient fields of an MRI machine are required for encoding the location during the image acquisition and are switched off outside of the image recording time. However, in principle, it is possible, in addition, to exert force on magnetic objects using the gradient fields. This is exploited within the scope of the present invention.

Within the scope of the invention, a counter force counter to the forces acting on a ferromagnetic particle may be provided with the aid of the magnetic field gradients. These forces acting on a ferromagnetic particle are applied to the particle outside of the measurement operation of an MRI system, in particular on account of gravity and liquid flows. In particular, a vertical magnetic counter force may be set with the aid of the gradients in such a way that the particle does not move downwards as a consequence of gravity. Furthermore, the particles may also be kept stationary should they be situated in a flowing medium. Furthermore, the particles may be moved in a controlled manner outside of the image recording time. Measurement procedures may be designed in such a way that gradients for holding and moving the particles are switched off during the spatial encoding of the data recording ("encoding time" of the MRI measurement sequence) in order not to interfere with the spatial encoding, but the magnetic particles are kept stationary on average or these are moved in a controlled manner when there is no spatial encoding of the data recording.

In particular, the invention proposes the application of a holding gradient; in general, this refers to a magnetic gradient which is applied outside of the measurement times in order to hold the magnetic particle in a stable position against a force acting on the particle. Firstly, this may be a vertical gradient (cf. gravitational counter field GG), which is directed against gravity. The strength of this gradient is set depending on the mass and the magnetization of the magnetic particle (both are known variables). Secondly, the holding gradient may act against a fluid flow, for example if the magnetic particle is situated within a moving fluid matrix (e.g. bloodstream). The field vector of the holding gradient (cf. flow counter field GF) should be selected depending on the magnitude and direction of this flow in this case, which is why a velocity profile is generally created first in the case of flows in order to determine the field vector of the gradient. Recording a velocity profile is known in the prior art (citation examples: Methods Mol. Biol. 2014; 1135:205-11: Quantitative cerebral blood flow measurements using MRI; and further Magn. Reson. Med. 2003 December; 50(6): 1248-1255: Real-Time Volumetric Flow Measurements With Complex-Difference MRI). It is also possible to configure combined holding gradients (GG and GF) against gravity and the flow profile. If external forces, such as e.g. gravity or the flow or else an unbalanced spatially encoding gradient switching operation, which act on the particles, move the particles significantly from the initial position during the encoding time, the particles may be moved back again by applying a compensation gradient. The strength and duration of the compensation gradient ("area") and the direction thereof need to be selected to be suitable for this, in particular depending on magnitude, direction and duration of the previously acting external forces.

According to the invention, the MRI measurement sequences are adapted in such a way that the magnetic objects are, on average, kept stationary. Furthermore, it is possible to apply additional gradient fields between the measurement sequences in order to move the magnetic particles in a controlled manner.

Measurement Sequences According to the Invention

Within the scope of the invention, a measurement sequence is subdivided into a multiplicity of measurement blocks. Each measurement block comprises an individual measurement (or else a plurality of individual measurements) and an intermediate gradient.

FIG. 1 shows a section of a measurement sequence with 2D individual measurements using the gradient echo (GRE) technique; here, time is plotted extending horizontally to the right and the RF signal or the respective switched gradient is plotted vertically. The section depicts a first individual measurement E1 and the start of a second individual measurement E2 in an exemplary manner. A measurement sequence typically comprises a multiplicity of further individual measurements. An individual measurement represents the recording of a single NMR signal in the case of a corresponding spatial encoding.

The totality of required individual measurements, for creating a complete image of the measurement volume or a sufficient selection of projections of the measurement volume so that the position of the ferromagnetic particle in the measurement volume is ascertainable, forms a measurement sequence.

In the variant shown in FIG. 1, each individual measurement is followed by a respective, so-called intermediate gradient ZW. Thus, the intermediate gradient ZW is applied in the measurement pause between two individual measurements E1, E2.

During the individual measurement E1, a radiofrequency (RF) pulse 1 ("excitation") is radiated into the measurement volume. After the encoding time, the RF signal 2 ("response") of the measurement volume is recorded. The spatially encoding gradients, in this case a slice-selection gradient GS, a readout gradient GR and a phase-encoding gradient GP, are switched during the individual measurement E1.

An additional gradient for holding or displacing the ferromagnetic particle would falsify the spatial encoding during the individual measurement E1, which is why such an additional gradient may only be applied outside of the encoding times. Therefore, the intermediate gradient ZW is applied exclusively here, between the individual measurements E1, E2. Accordingly, there typically is a certain amount of drift of the ferromagnetic particle during the individual measurement E1.

In this case, the intermediate gradient ZW comprises a gravitational counter field GG, which exactly compensates the (current) effect of gravity, as a first component. The force resulting from the vertical gravitational counter field GG is counter to the gravitational force and is sufficiently strong that the ferromagnetic particle is held floating (vertically) in the measurement volume. The intermediate gradient ZW additionally includes, as a second component, a flow counter field GF, which compensates for the (current) effect of a liquid flow. The force resulting from the flow counter field GF is counter to the action of force of the liquid flow in the liquid matrix, to which the particle is exposed, and is so strong that the particle is not moved by the liquid flow. It should be noted that the flow counter field GF may, in principle, be directed in any spatial direction, depending on the flow conditions. The flow conditions should accordingly be known as exactly as possible in order to obtain a compensation which is as exact as possible. The particle would be held at a constant position ("holding gradient") between the individual measurements E1 and E2 through the gravitational counter field GG and the flow counter field GF only. Furthermore, the intermediate gradient ZW comprises here, as a third component, a gradient field GZ for pushing the ferromagnetic particle back to the position at the start of the individual measurement E1. This ensures that the individual measurement E1 and the individual measurement E2 each start with the particle at the same position and so all individual measurements E1, E2 fit to one another. Thus, the drop of the particle on account of gravity and the carrying along of the particle on account of the flow during the individual measurement E1 are compensated ("compensation gradient"), or "undone", by the gradient field GZ. In the shown embodiment, the gradient field GZ acts during the entire intermediate gradient; alternatively, the gradient field GZ may also act during only a part of the intermediate gradient. The duration of the gradient field GZ is directed to the amount of time required to compensate the drift from the individual measurement.

The first individual measurement E1 and the intermediate gradient ZW form a first measurement block MB1 of the measurement sequence. A second measurement block MB2 of the measurement sequence starts with the individual measurement E2. Here, the individual measurement E2 may not start until after the repetition time TR has elapsed, the latter ensuring a sufficient relaxation of the nuclear spins in the measurement volume.

In the case of a 2D gradient echo sequence, the excitation pulse (RF pulse 1) is followed by a dephasing gradient switching operation (cf., in particular, readout gradient GR). The return of the phase shift in the readout direction and hence the generation of the gradient echo is achieved by reversing the readout gradient GR.

The variant of FIG. 1 shows a balanced gradient echo sequence; i.e., in terms of the action thereof, the gradients GS, GR and GP cancel over the individual measurement E1 such that they have no influence on the position of the particle after completion of the individual measurement E1. To this end, respectively mutually corresponding switching blocks 3a, 3b and 4a, 4b and 5a, 5b of the gradients GS, GR and GP are provided after the inward radiation of the RF pulse 1 and after recording the echo signal, i.e. the RF signal 2.

Figure 2:
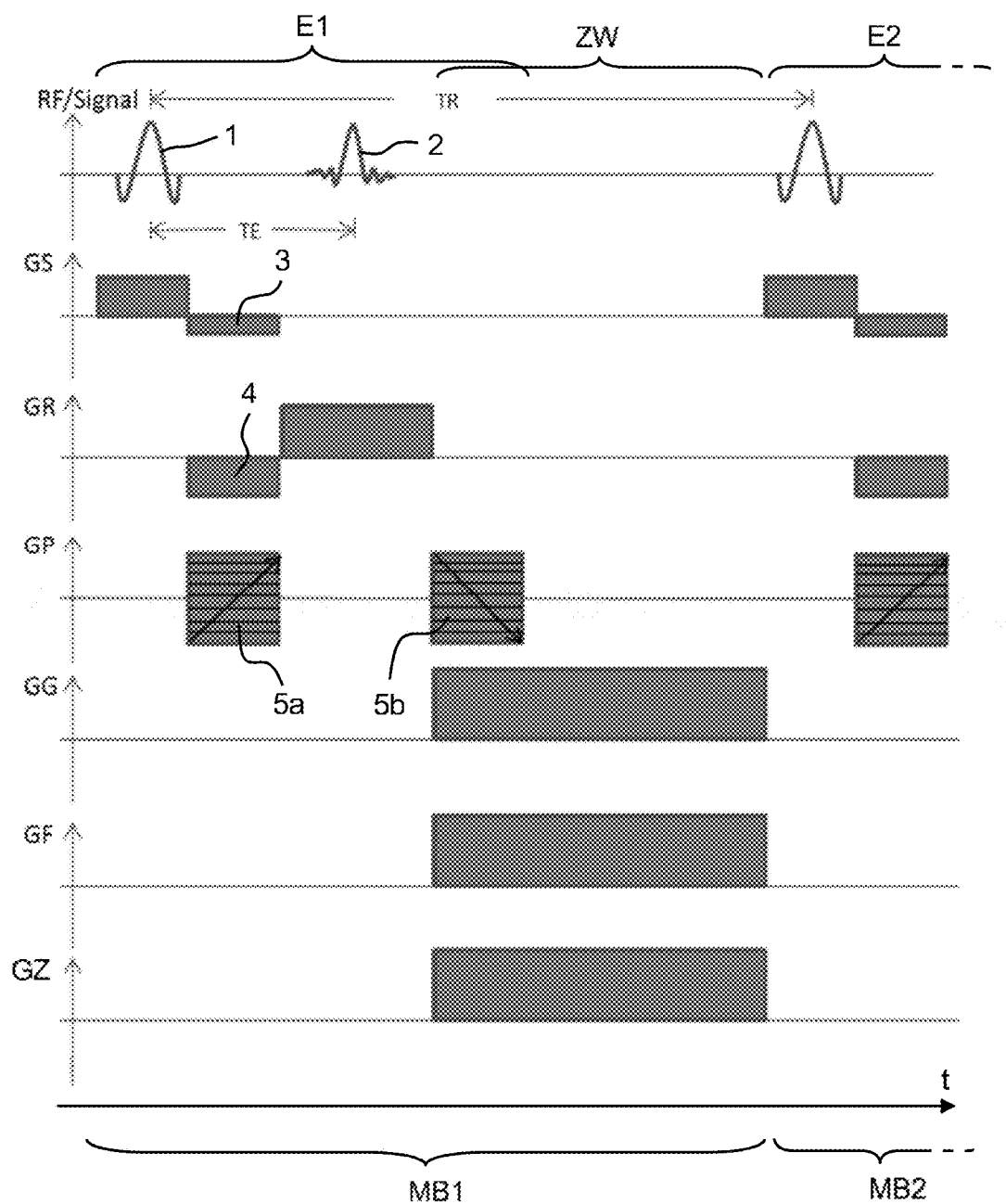
FIG. 2 shows a schematic illustration of applied gradients during a measurement sequence within the scope of the invention, in a variant with an unbalanced gradient switching operation.

The variant of FIG. 2, which corresponds in large part to the variant of FIG. 1, shows an unbalanced gradient echo sequence. The readout gradient GR and the slice selection gradient GS are not self-compensated; the switching blocks 3, 4 after the RF pulse 1 do not find correspondence after recording the RF signal 2. Here, the compensation is carried out via the intermediate gradient ZW, in particular via the gradient field GZ. This is particularly advantageous if the readout gradient GR or the slice selection gradient GS are directed, in any case, in the y-direction (vertical direction), i.e. in the direction of gravity. A drift of the particle as a result of the unbalanced gradient echo switching operation during the individual measurement E1 is also compensated by a corresponding push-back of the particle via the intermediate gradient ZW or its component of the gradient field GZ. It should be noted that a small overlap between individual measurement E1 and intermediate gradient ZW is provided in this variant, namely during the second block 5b of the phase-encoding gradient GP. This overlap is non-critical since the recording of the RF signal 2 has already been completed. In this example, the part 5b of the phase-encoding gradient serves for cancelling the encoding by the gradient 5a and may be switched simultaneously with the intermediate gradient.

In the illustrated method, the intermediate gradient ZW, in particular with the holding gradients (i.e. the gravitational counter field GG and the flow counter field GF), acts as a spoiler which dephases the nuclear spins.

Figure 3A:
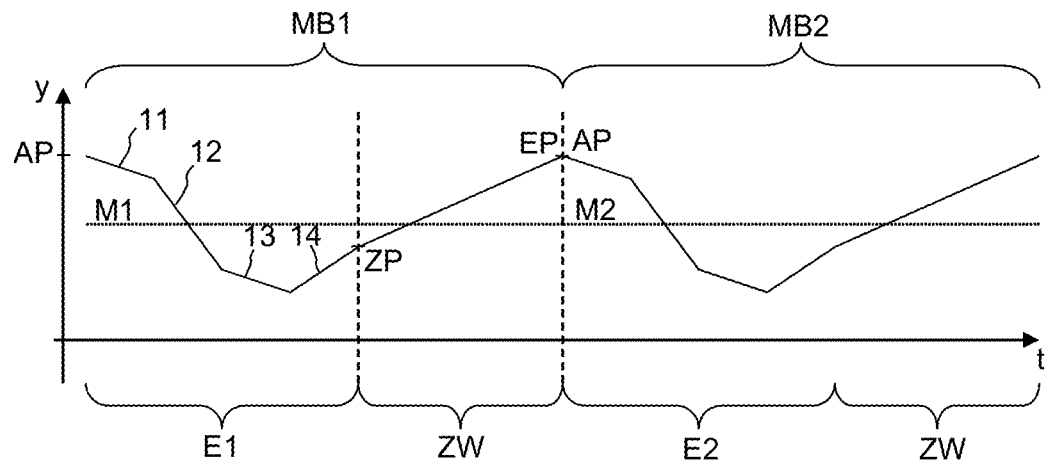
FIG. 3A shows a schematic illustration of the position of a ferromagnetic particle during a measurement sequence within the scope of the invention, in a variant with a pushback of the particle by the intermediate gradient.

In a diagram, FIG. 3A elucidates the position of a ferromagnetic particle in the vertical y-direction (plotted vertically) as a function of time t (plotted horizontally) over a section of a measurement sequence within the scope of the invention, comprising a push-back of the particle. Here, the section comprises, by way of example, two measurement blocks MB1, MB2.

In the absence of magnetic field gradients, the particle drops significantly (in the −y direction) on account of gravity, as in the time intervals 11 and 13 of the individual measurement E1, particularly if the viscosity of the liquid matrix is low and/or the mass of the particle is high. A spatially encoding gradient switching operation is effective intermittently during the individual measurement E1. In this case, this accelerates the drop over the time interval 12 and brings about slight rising of the particle over the time interval 14 ("balanced gradient switching operation"). The effect of gravity overall causes a drop of the particle from the initial point AP to the intermediate point ZP over the individual measurement E1.

According to the invention, an intermediate gradient ZW is now applied during a measurement pause (pause of the spatial encoding between E1 and E2). During the duration of the intermediate gradient ZW, said intermediate gradient pulls the particle upwards again (in the y-direction) to an end point EP from the intermediate point ZP. The end point EP is (at least substantially) equal to the initial point AP, i.e. the entire drift over the measurement block MB1 in the y-direction is ideally "zero". Accordingly, the next individual measurement E2 with the particle may start again at approximately the same initial point AP. Then, in respect of the position of the particle in the y-direction over time t, the profile of the second individual measurement E2 corresponds to the profile of the first individual measurement E1.

The position of the particle may be averaged (in respect of the y-direction) over the entire first measurement block MB1. The mean position M1 emerges. The position of the particle may likewise be averaged over the entire measurement block MB2, with the mean position M2 emerging. The mean positions M1 and M2 are (substantially) the same on account of the (substantially) same initial points AP at the start of the measurement blocks MB1, MB2, which proceed in the same manner.

It should be noted that the particle within the scope of the invention may drift in up to three dimensions and said particle is compensated accordingly in up to three dimensions via the intermediate gradient, even though only one dimension is illustrated in more detail in FIG. 3A for simplification purposes.

Figure 3B:
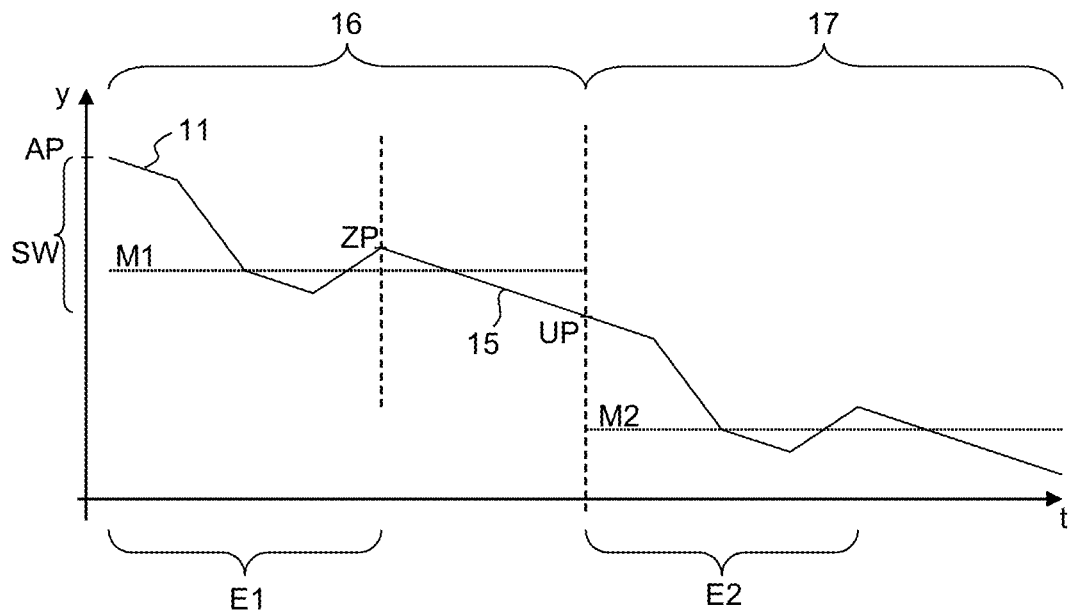
FIG. 3B shows a schematic illustration of the position of a ferromagnetic particle during a measurement sequence similar to FIG. 3A, but without the application of an intermediate gradient (not inventive)

In contrast thereto, FIG. 3B shows a section of a corresponding measurement sequence, wherein no intermediate gradient is switched between the individual measurements E1, E2, but there simply is waiting instead (not inventive). After the individual measurement E1, the particle drops freely on account of gravity in the time interval 15, with the same velocity as in the time interval 11. Accordingly, the particle drops from the intermediate point ZP to the non-compensated point UP, which lies below the initial point AP by a drop path SW. The next individual measurement E2, which proceeds analogously to the individual measurement E1, starts from said non-compensated point UP. Then, the mean position M1 of the particle over the time interval 16 (from the start of the first individual measurement E1 to the start of the next individual measurement E2) is higher by the drop path SW than the mean position M2 over the time interval 17 of equal length, which starts with the further individual measurement E2.

Figure 4A:
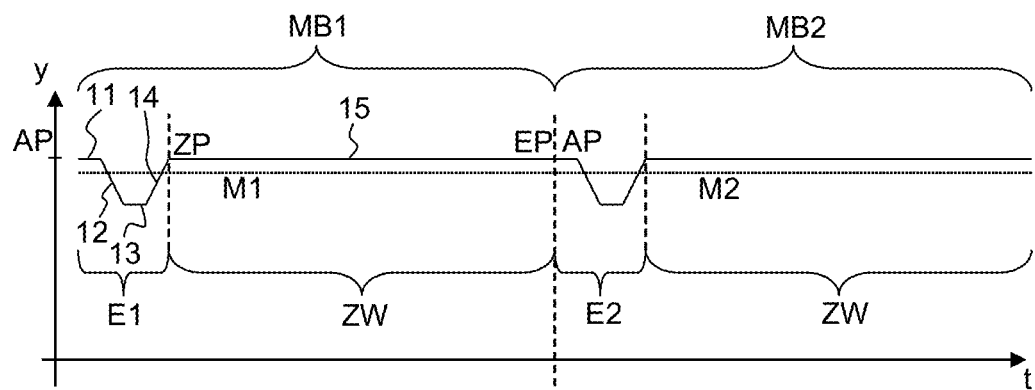
FIG. 4A shows a schematic illustration of the position of a ferromagnetic particle during a measurement sequence within the scope of the invention, in a variant with the particle only being held by the intermediate gradient.

In a diagram, FIG. 4A explains the position of a ferromagnetic particle in the vertical y-direction (plotted vertically) as a function of time t (plotted horizontally) over a section of a measurement sequence within the scope of the invention, comprising a holding of the particle. Here too, the section comprises, by way of example, two measurement blocks MB1, MB2.

In this variant, the individual measurement E1 is relatively short in comparison with the associated total measurement block MB1, the viscosity of the liquid matrix is high and/or the mass of the particle is low, and so there is no noticeable change in position as a result of gravity during E1, in particular not during the time intervals 11, 13 either. The changes in position in the time intervals 12, 14 on account of the spatially encoding gradient switching operation cancel ("balanced gradient switching operation"). Accordingly, the location of the particle at the end of the first individual measurement E1, i.e. the intermediate point ZP, is approximately equal to the initial point AP.

In the measurement pause between the first individual measurement E1 and second individual measurement E2, an intermediate gradient ZW is now applied in such a way that it holds the particle precisely in position in relation to the y-direction. To this end, the particle may be pressed against a close-by edge structure, which delimits the liquid matrix, under the application of a contact gradient (also denoted GA). Alternatively, the applied intermediate gradient ZW comprising gravitational counter field and, optionally, flow counter field, may also just compensate the external forces on the particle. At the end of the duration of action of the intermediate gradient ZW, the particle is situated at the end point EP, which approximately corresponds to the intermediate point ZP and the initial point AP.

Accordingly, the next individual measurement E2 with the particle may approximately start at the same initial point AP again. Then, in respect of the position of the particle in the y-direction over time t, the profile of the second individual measurement E2 corresponds to the profile of the first individual measurement E1. The mean positions M1 and M2 in the first measurement block MB1 and in the second measurement block MB2 are approximately equal.

Figure 4B:
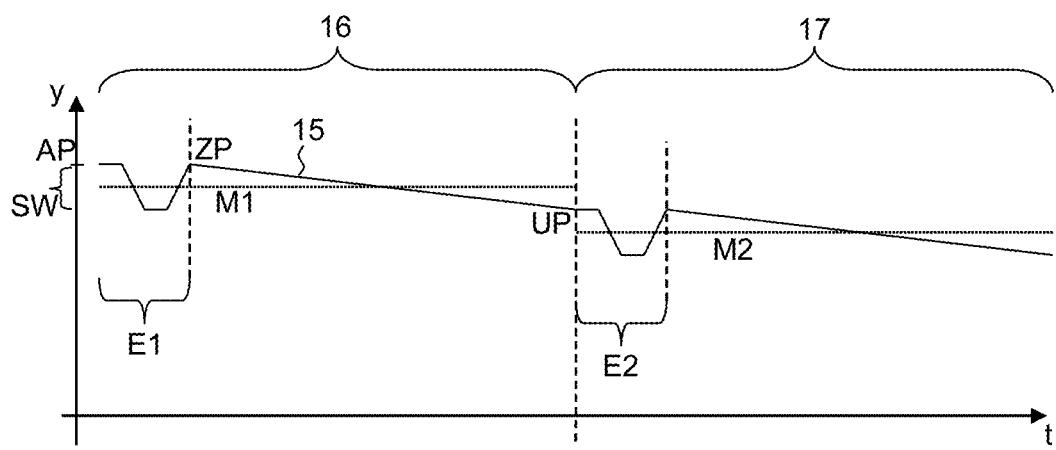
FIG. 4B shows a schematic illustration of the position of a ferromagnetic particle during a measurement sequence similar to FIG. 4A, but without the application of an intermediate gradient (not inventive)

In contrast thereto, FIG. 4B once again shows a section of a corresponding measurement sequence, wherein no intermediate gradient is switched between the individual measurements E1, E2, but there simply is waiting instead (not inventive). After the individual measurement E1, the particle drops freely to a slight extent in the time interval 15 on account of gravity. Accordingly, the particle drops from the intermediate point ZP to the non-compensated point UP, which lies below the initial point AP by a drop path SW. The next individual measurement E2, which proceeds analogously to the individual measurement E1, starts from this non-compensated point UP. Then, the mean position M1 of the particle over the time interval 16 (from the start of the first individual measurement E1 to the start of the next individual measurement E2) is higher by the drop path SW than the mean position M2 over the time interval 17 of equal length, which starts with the further individual measurement E2.

Displacing the Particle Between Measurement Sequences

Determining the position of a particle in the liquid matrix with a measurement sequence described above is generally carried out in order to position the particle at a desired location in the liquid matrix or in the measurement volume and in order, in the process, to monitor the position after the respective iterative partial steps of displacing the particle.

The MRI system used to localize and position the ferromagnetic particle should generate a homogeneous magnetic field (B0 field) in the measurement volume such that the particle does not experience any location-displacing forces as a result of magnetism (without applying the gradient coil system); an alignment of the particle in the B0 field is unavoidable.

In general, a complete measurement sequence needs to be carried out in order to obtain the spatial information allowing the determination of the position of the particle in the measurement volume.

If the particle should be conveyed on to a specific point, it is necessary to switch a positioning gradient which moves the particle in a predetermined direction. Preferably, the positioning gradient is composed of a holding gradient (which, on its own, would hold the position of the particle constant against gravity and/or the liquid flow) and an additional displacement gradient (which causes the actual displacement and is also denoted GV) in order to be able to control the particle displacement more easily. The strength of the positioning gradient (or of the displacement gradient) and the duration of the actuation of the positioning gradient (or of the displacement gradient) are adapted to the path to be traveled.

Figure 5:
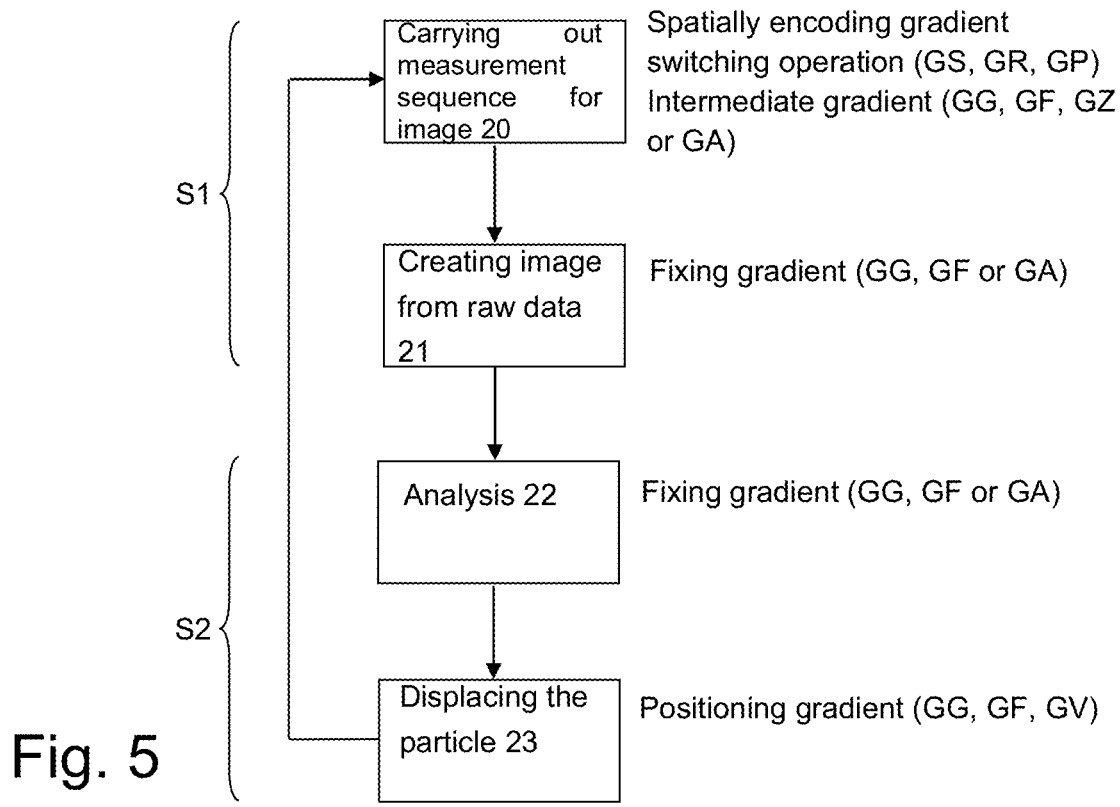
FIG. 5 shows a schematic flow chart of a variant of the method according to the invention for changing the position of a ferromagnetic particle.

FIG. 5 shows a schematic illustration of the procedure of a variant of the imaging Mill method according to the invention, by which a magnetic particle is controlled at the same time.

In a first step S1 (determining the position of the particle), the method comprises carrying out a measurement sequence for an image 20 of the measurement volume and creating the image 21 from the raw data of the individual measurements of the measurement sequence and, in a second step S2 (changing the position of the particle), said method initially comprises an analysis 22, by which the next displacement step is planned and set, and the actual displacement of the particle 23. Subsequently, the position of the particle is monitored again and modified, et cetera, until the desired location in the liquid matrix has been reached. The right-hand side of FIG. 5 specifies the types of gradient to be applied, which are switched for the corresponding partial steps 20, 21, 22, 23. Here, the fixing gradient during the partial steps 21, 22 is either embodied as a holding gradient (with GG, GF, which exactly compensates gravity and, optionally, the liquid flow) or as a contact gradient (GA, which holds the particle on an edge structure).

Figure 6:
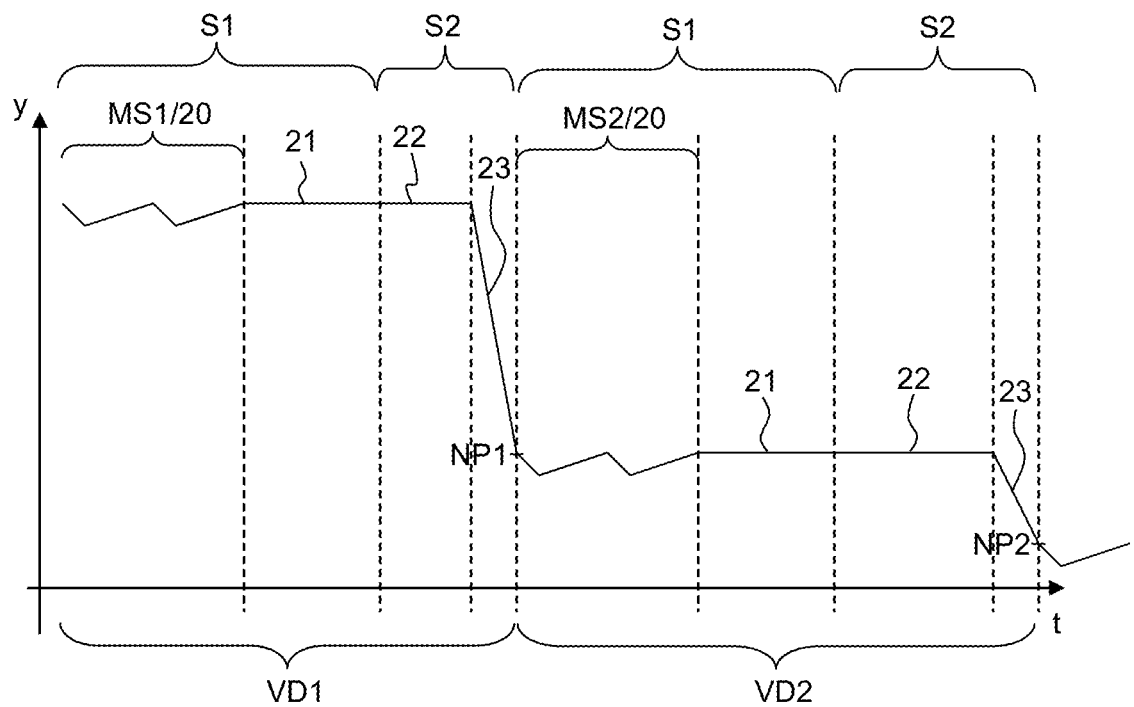
FIG. 6 shows a schematic illustration of the position of a ferromagnetic particle during a variant of the method according to the invention for changing the position of the ferromagnetic particle.

In a diagram, FIG. 6 illustrates the repositioning of a ferromagnetic particle using an MRI system in accordance with the invention. A spatial coordinate, in this case the vertical y-direction, is plotted vertically and time t is plotted horizontally.

In a first method iteration VD1, the raw data for an image of the measurement volume are recorded in a first measurement sequence MS1, 20. Here, the position of the particle varies within the individual measurement blocks of the measurement sequence MS1. However, the mean position of the particle is the same for each one of the measurement blocks. The position of the particle remains the same under the action of the fixing gradient while the image 21 is created from the raw data of the individual measurements. Now, the current location of the particle is known for the subsequent analysis 22, and so a next displacement (approach to the target location) may be planned. The position of the particle remains constant during the analysis 22 under the further action of the fixing gradient. During the subsequent displacement of the particle 23, the latter is brought to a new position NP1. The latter is checked in the now subsequent second method iteration VD2, and a further displacement of the particle to the new position NP2 is carried out. This is adjoined by a further method iteration, et cetera, until the desired target location has been reached.

It should be noted that the particle is displaced in up to three dimensions within the scope of the invention, even though only one dimension is illustrated in more detail in FIG. 6 for simplification purposes.

FIGS. 7A-7D illustrate exemplary force conditions on a particle and the movement thereof in a liquid matrix with an edge structure during various method stages in accordance with the invention.

Figure 7A:
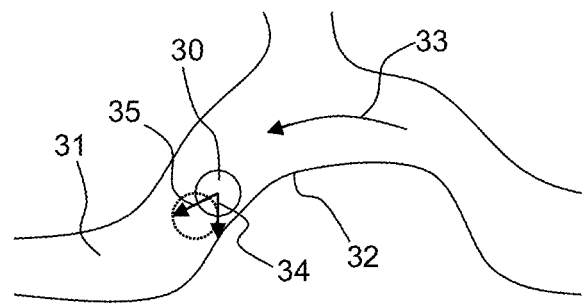
FIGS. 7A-7D show schematic illustrations of a ferromagnetic particle in a liquid matrix within a surrounding edge structure, during an individual measurement (FIG. 7A), during the application of an intermediate gradient (FIG. 7B), during the application of a fixing gradient (FIG. 7C) and during the application of a positioning gradient (FIG. 7D)

As may be identified in FIG. 7A, a ferromagnetic particle 30, illustrated here to be approximately spherical, is arranged in a liquid matrix 31 in this case. The liquid matrix 31 is enclosed by an edge structure (illustrated here as walls of channels). The liquid matrix 31 is subject to a flow 33.

The particle 30 is pulled downwards by gravity 34 and is driven substantially along the course of the channel by the action of the flow 35. During an individual measurement (which here, on its own, does not change the position on account of a balanced gradient switching operation), these external forces lead to a displacement of the particle 30 to the position denoted by the dotted sphere.

Figure 7B:
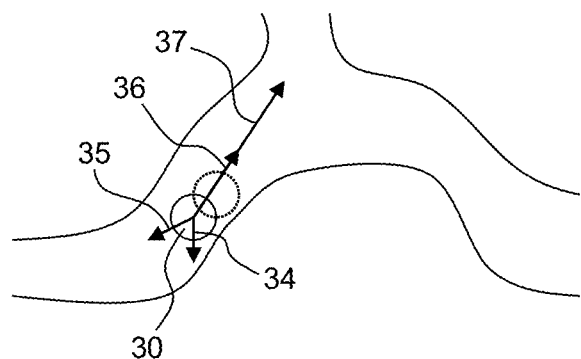

It is for this reason that, according to the invention, an intermediate gradient is switched after the individual measurement, cf. FIG. 7B. A first component 36 of the action thereof counteracts gravity 34 and the action of the flow 35 during the duration of action thereof ("holding gradient"). A further component 37 of the action thereof pulls the particle 30 back to the preceding position at the start of the individual measurement.

Individual measurement and intermediate gradient alternate many times during a measurement sequence.

Figure 7C:
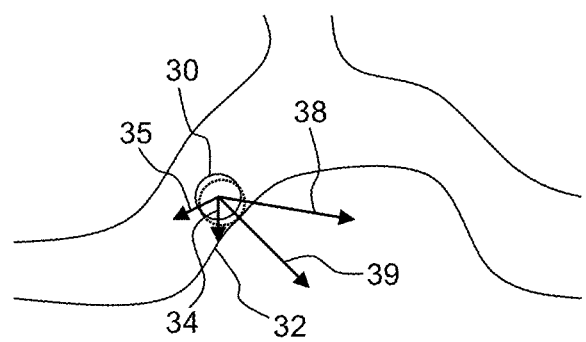

After completion of the measurement sequence, the particle 30 should be held in a stationary manner, cf. FIG. 7C, for example for an image calculation and an analysis for the further procedure. In the shown variant, a fixing gradient is switched to this end, said fixing gradient in this case being selected as contact gradient. The action of force 38 thereof is partly cancelled by the action of gravity 34 and the action of the flow 35. The resultant (remaining) force 39 pulls the particle 30 approximately perpendicularly to the local surface of the closest part of the edge structure 32. It should be noted that the action of gravity 34 must be known (but which is readily determined from the volume of the particle, the density of the particle material and the density of the liquid matrix for taking into account buoyancy) for setting the fixing gradient. In addition, the action of the flow must be known (this is readily determined as well, from the size of the particle, the viscosity of the liquid matrix and the flow profile. The flow profile may be determined in advance without the particle by way of MRI) and, furthermore, the position of the edge structure must be known (ascertainable from a preceding MRI image recording).

Figure 7D:
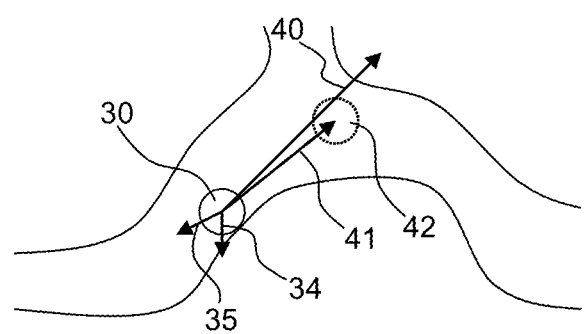

After analysing the further procedure, it is now possible to displace the particle 30, cf. FIG. 7D. To this end, a positioning gradient is applied. The action of force 40 thereof serves partly to compensate gravity 34 and the action of the flow 35 ("holding gradient" component). The remaining action of force 41 ("displacement gradient" component) displaces the particle to a new position 42.

Thereupon, it is possible to undertake a further position determination and position displacement, et cetera.

Figure 8:
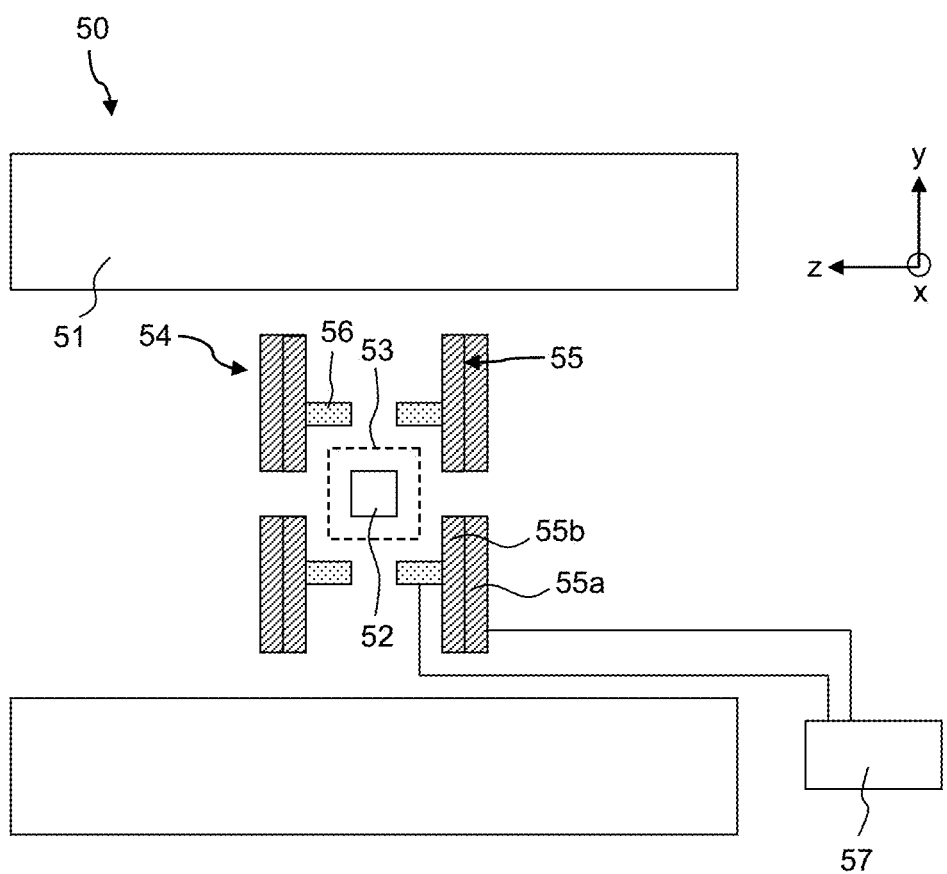
FIG. 8 shows a schematic illustration of an MRI system according to the invention.

FIG. 8 shows an embodiment of an MRI system 50 according to the invention, in particular for carrying out a position determination and/or change in position of a ferromagnetic particle (object) within the scope of the invention.

The MRI system 50 comprises a magnet (main magnetic coil system, typically superconducting) 51, with which it is possible, in a measurement volume 52, to generate a strong, homogeneous magnetic field B0 in the horizontal z-direction, typically with a strength of 1 T or more. Using a radiofrequency excitation and readout coil system 53, it is possible to radiate RF pulses into the measurement volume 52 and readout an RF signal from the measurement volume. Furthermore, a gradient coil system 54 is provided, with which magnetic field gradients may be generated in the measurement volume 52.

In this case, the gradient coil system 54 comprises a first coil subsystem 55, with which magnetic field gradients may be generated in a vertical y-direction, i.e. the magnetic field strength changes along the y-direction. Furthermore, provision is made of a second coil subsystem 56, with which magnetic field gradients may be generated in the horizontal z-direction, i.e. the magnetic field strength changes along the z-direction.

Here, the first coil subsystem 55 has a significantly stronger embodiment than the second coil subsystem 56, for example for a gradient strength which is greater by at least 1.5 times, such that even a significant gravitational force on a ferromagnetic particle in the y-direction may be compensated without problems. Here, the first coil subsystem 55 is configured with a main part 55a and an additional part 55b which is situated on the interior in this case. The additional part 55b is only used if, at least, an action of gravity should also be compensated (i.e. in the case of intermediate gradients, fixing gradients and positioning gradients), but not for a spatially encoding gradient switching operation. The main part is used to undertake spatially encoding gradient switching operations. It may further be used to compensate an action of gravity (i.e. for intermediate gradients, fixing gradients and positioning gradients).

The gradient coil system 54 is controlled by way of an electronic control device 57 which is programmed to switch intermediate gradients between individual measurements or groups of individual measurements of a measurement sequence and to switch fixing gradients and positioning gradients between measurement sequences.

LIST OF REFERENCE SIGNS

1 RF pulse (excitation)
2 RF signal (response)
3 Non-compensated switching block (GS)
3a, 3b Compensated switching blocks (GS)
4 Non-compensated switching block (GR)
4a, 4b Compensated switching blocks (GR)
5a, 5b Compensated switching blocks (GP)
11-14 Time intervals during an individual measurement
15 Time interval after an individual measurement
16, 17 Time intervals from the start of an individual measurement to the start of the next individual measurement
20 Carrying out the measurement sequence for an image
21 Creating an image from raw data
22 Analysis
23 Displacement of the particle
30 Ferromagnetic particle (object)
31 Liquid matrix
32 Edge structure
33 Flow
34 Gravity (force)
35 Action of flow (force)
36 First component of the action of the intermediate gradient (force)
37 Second component of the action of the intermediate gradient (force)
38 Effect of the contact gradient (force)
39 Resultant force
40 Action of force of the positioning gradient (force)
41 Remaining action of force (force)
42 New position of the particle
50 MRI system
51 Magnet
52 Measurement volume
53 Radiofrequency excitation and readout coil system
54 Gradient coil system
55 First coil subsystem
55a Main part
55b Additional part
56 Second coil subsystem
57 Control device
AP Initial point
E1 First individual measurement
E2 Second individual measurement
EP End point
GA Contact gradient
GF Flow counter field (gradient)
GG Gravitational counter field (gradient)
GP Phase-encoding gradient
GR Readout gradient
GS Slice selection gradient
GV Displacement gradient
GZ Gradient field for pushing back the ferromagnetic particle (gradient)
M1 Mean position during the first measurement block
M2 Mean position during the second measurement block
MB1 First measurement block
MB2 Second measurement block
MS1 First measurement sequence
MS2 Second measurement sequence
NP1 First new position
NP2 Second new position
SW Drop path
S1 Step 1
S2 Step 2
t Time
TE Echo time
UP Non-compensated point
x Horizontal direction
y Vertical direction
VD1 First method iteration
VD2 Second method iteration
z Horizontal direction
ZP Intermediate point
ZW Intermediate gradient

What is claimed is:

1. Method for determining a position of at least one ferromagnetic particle in a liquid matrix with an MRI system, comprising:
applying an MRI measurement sequence to a measurement volume in which the particle is situated, wherein the measurement sequence comprises a plurality of individual measurements, during each of which there is a spatially encoding gradient switching operation, including an excitation pulse and a signal recording with the MRI system, and wherein the measurement sequence further comprises a multiplicity of measurement blocks, each of which comprises at least one individual measurement and each of which, in a pause of the spatial encoding, comprises an intermediate gradient switched by the MRI system; and
dimensioning the intermediate gradient such that, over each of the measurement blocks, an initial point of the particle is substantially the same as an end point of the particle.

2. Method according to claim 1, wherein the particle moves away from the initial point during the at least one individual measurement during a respective measurement block, and
further comprising dimensioning the intermediate gradient such that, during action of the intermediate gradient, the particle moves back at least approximately to the initial point.

3. Method according to claim 2, wherein the particle moves under influence of gravity and/or a flow of the liquid matrix and/or action of the spatially encoding gradient switching operation during the at least one individual measurement.

4. Method according to claim 1, wherein the spatially encoding gradient switching operation is balanced in such a manner that, in total, the operation does not contribute to a change in position of the particle during the individual measurement.

5. Method according to claim 1, wherein the spatially encoding gradient switching operation is unbalanced in such a manner that the operation contributes to a change in position of the particle during the individual measurement, and wherein the intermediate gradients also compensate the contributions of the spatially encoding gradient switching operation.

6. Method according to claim 1, further comprising measuring flows in the liquid matrix prior to applying the measurement sequence, wherein said measurement renders a contribution of the flows to a change in position of the particle during the individual measurement and/or during a pause of the spatial encoding ascertainable, and wherein the intermediate gradients also compensate the contributions of the flows.

7. Method according to claim 1, wherein the intermediate gradient, at least intermittently, presses the particle against an edge structure neighbouring the liquid matrix.

8. Method according to claim 1, wherein only one individual measurement is carried out during each measurement block.

9. Method according to claim 1, further comprising generating a complete image of the measurement volume from the results of the individual measurements of the measurement sequence.

10. Method according to claim 1, further comprising:
creating a multiplicity of reference projections of the measurement volume without the particle prior to the measurement sequence,
recording a multiplicity of projections of the measurement volume with the particle via the individual measurements, and
ascertaining the position of the particle by comparison between the recorded projections and the reference projections.

11. Method for positioning at least one ferromagnetic particle in a liquid matrix with an MM system, comprising:
determining the position of the particle with the MRI system; and
switching a positioning gradient with the MRI system, thereby changing a position of the particle,
wherein said determining step comprises said method according to claim 1 performed with a fixing gradient as the intermediate gradient, whereby the position of the particle is kept at least substantially constant, and
wherein said switching step with the MRI system is performed following application of the measurement sequence in said determining step and until start of the application of the positioning gradient in said switching step.

12. Method according to claim 11, further comprising repeating said determining and switching steps multiple times.

13. Method according to claim 11, wherein the particle experiences a force under action of the fixing gradient, said force being equal and opposite to the action of gravity and/or the action of a flow of the liquid matrix.

14. Method according to claim 11, wherein the fixing gradient presses the particle against an edge structure neighbouring the liquid matrix.

15. Magnetic resonance imaging (MRI) system, comprising:
a magnet for generating a homogeneous magnetic field $B_0$ in a measurement volume,
a gradient coil system for generating spatially encoding magnetic field gradients in the measurement volume,
a radiofrequency excitation and readout coil system for radiating radiofrequency pulses into the measurement volume and for reading the measurement volume, and
a control device,
wherein the MRI system is configured to determine a position of a ferromagnetic particle in a liquid matrix,
wherein the determination comprises:
applying an MRI measurement sequence to the measurement volume, wherein the measurement sequence comprises a plurality of individual measurements, during each of which there is a spatially encoding gradient switching operation, including an excitation pulse and a signal recording with the MRI system, and wherein the measurement sequence further comprises a multiplicity of measurement blocks, each of which comprises at least one individual measurement and each of which, in a pause of the spatial encoding, comprises an intermediate gradient switched by the MRI system, and
dimensioning the intermediate gradient such that, over each of the measurement blocks, an initial point of the particle is substantially the same as an end point of the particle,
wherein the control device is configured to switch the intermediate gradients between the individual measurements of the measurement sequence via the gradient coil system,
wherein the MRI system is further configured to position the ferromagnetic particle in the liquid matrix
wherein the positioning comprises:
switching a positioning gradient with the MRI system, thereby changing the position of the particle, and
again performing the determination with a fixing gradient as the intermediate gradient, whereby the position of the particle is kept at least substantially constant, and
wherein said switching step is performed following application of the measurement sequence in said again performing step and until start of the application of the positioning gradient in said switching step, and
wherein the control device, via the gradient coil system, switches fixing gradients between the end of measurement sequences and application of the positioning gradients.

16. MRI system according to claim 15, wherein the gradient coil system of the MRI system comprises a first coil subsystem for generating a magnetic field gradient in a vertical direction (y) and at least one second coil subsystem for generating a magnetic field gradient in a horizontal direction (z, x), and
wherein the first coil subsystem has a maximum generable gradient strength $|G_{max}^1|$ which is greater than a maximum generable gradient strength $|G_{max}^2|$ of the second coil subsystem.

17. MRI system according to claim 16, wherein the first coil subsystem of the gradient coil system comprises a main part and an additional part, wherein the control device is configured to switch spatially encoding gradient switching operations, intermediate gradients, fixing gradients and/or positioning gradients with the main part, and wherein the control device is further configured to switch intermediate gradients, fixing gradients and/or positioning gradients, but not spatially encoding gradient switching operations, with the additional part.

18. Method according to claim 6, wherein the flows in the liquid matrix are measured prior to introducing the particle into the liquid matrix.

19. Method according to claim 10, wherein the multiplicity of reference projections of the measurement volume are created by directly recording the reference projections of the measurement volume without the particle or by calculating from a complete image recording of the measurement volume without the particle.

20. MRI system as claimed in claim 16, wherein $|G_{max}^1| \geq 1.5 * |G_{max}^2|$.

\* \* \* \* \*